United States Patent [19]
Brouwer et al.

[11] Patent Number: 5,914,351
[45] Date of Patent: Jun. 22, 1999

[54] ANTI-VIRAL AROMATIC HYDRAZONES

[75] Inventors: Walter Gerhard Brouwer, Guelph; Ewa Maria Osika, Kitchener, both of Canada

[73] Assignees: Uniroyal Chemical Company, Inc., Middlebury, Conn.; Uniroyal Chemical Co./CIE., Elmira, Canada

[21] Appl. No.: 08/989,377

[22] Filed: Dec. 12, 1997

[51] Int. Cl.$^6$ .......................... A61K 31/15; A61K 31/16; A61K 31/34; A61K 31/40; A61K 31/535; A61K 31/66; C07D 265/30; C07D 207/50; C07D 307/02; C07F 9/02; C07C 327/00; C07C 241/00; C07C 243/00; C07C 249/00; C07C 251/00

[52] U.S. Cl. .......................... 514/639; 514/63; 514/85; 514/86; 514/89; 514/90; 514/91; 514/92; 514/94; 514/118; 514/183; 514/211; 514/212; 514/218; 514/222.5; 514/226.8; 514/227.5; 514/227.8; 514/231.5; 514/231.8; 514/235.5; 514/235.8; 514/236.8; 514/237.8; 514/238.8; 514/252; 514/255; 514/256; 514/316; 514/326; 514/329; 514/362; 514/363; 514/364; 514/365; 514/372; 514/374; 514/378; 514/397; 514/399; 514/406; 514/422; 514/423; 514/426; 514/433; 514/436; 514/448; 514/452; 514/459; 514/461; 514/471; 514/599; 514/614; 540/467; 540/470; 540/480; 540/481; 540/482; 540/542; 540/544; 540/553; 540/575; 540/597; 540/598; 540/601; 540/602; 540/603; 540/605; 544/2; 544/53; 544/57; 544/59; 544/60; 544/62; 544/69; 544/86; 544/88; 544/96; 544/111; 544/121; 544/122; 544/129; 544/133; 544/137; 544/138; 544/139; 544/140; 544/141; 544/143; 544/145; 544/146; 544/147; 544/148; 544/149; 544/152; 544/157; 544/164; 544/229; 544/243; 544/295; 544/296; 544/322; 544/337; 544/357; 544/360; 544/367; 544/369; 544/370; 544/371; 544/372; 544/373; 544/374; 544/379; 544/382; 546/14; 546/22; 546/190; 546/201; 546/208; 546/209; 546/210; 546/211; 546/213; 546/214; 546/223; 548/110; 548/112; 548/127; 548/128; 548/131; 548/134; 548/136; 548/143; 548/200; 548/204; 548/214; 548/236; 548/248; 548/314.7; 548/333.5; 548/336.1; 548/364.1; 548/374.1; 548/406; 548/413; 548/492; 548/494; 548/517; 548/518; 548/527; 548/537; 548/557; 549/4; 549/14; 549/22; 549/72; 549/214; 549/378; 549/425; 549/487; 564/12; 564/74; 564/147; 564/251

[58] Field of Search .................... 540/467, 470, 540/480, 481, 482, 542, 544, 553, 575, 597, 598, 601, 602, 603, 605; 544/2.53, 57, 59, 60, 62, 69, 86, 88, 96, 111, 121, 122, 129, 133, 137, 138, 139, 140, 141, 143, 145, 146, 147, 148, 149, 152, 157, 164, 229, 243, 295, 296, 322, 337, 357, 360, 367, 369, 370, 371, 372, 373, 374, 379, 382; 546/14, 22, 190, 201, 208, 209, 210, 211, 213, 214, 223; 548/110, 112, 127, 128, 131, 134, 136, 143, 200, 204, 214, 236, 248, 314.7, 333.5, 336.1, 364.1, 374.1, 406, 413, 492, 494, 517, 518, 527, 537, 557; 549/4, 14, 22, 72, 214, 378, 425, 487; 564/12, 74, 147, 251; 514/63, 85, 86, 89, 90, 91, 92, 94, 118, 183, 211, 218, 222.5, 226.8, 227.5, 227.8, 231.5, 231.8, 235.5, 235.8, 236.8, 237.8, 238.8, 252, 255, 256, 316, 326, 329, 362, 363, 364, 365, 372, 374, 378, 397, 399, 406, 422, 423, 426, 433, 436, 448, 452, 459, 461, 471, 599, 614, 639

[56] References Cited

U.S. PATENT DOCUMENTS 5,268,389 12/1993 Harrison .................................. 514/485

*Primary Examiner*—Richard L. Raymond
*Assistant Examiner*—Brenda Coleman
*Attorney, Agent, or Firm*—Daniel Reitenbach

[57] ABSTRACT

Compounds of the formula

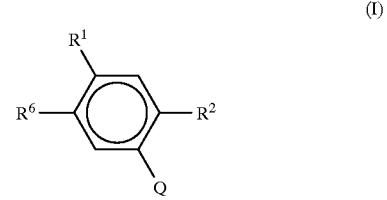

wherein
  Q is a hydrazone derivative;
  $R^1$ is hydrogen, halogen, alkyl or alkoxy;
  $R^2$ is hydrogen, halogen, alkyl, alkoxy, alkenoxy, alkynyloxy, halomethyl, trifluoromethoxy, alkylthio, nitro or cyano; and
  $R^6$ is a substituted carboxamide, carbothioamide, phosphonosoamide, or phosphonothioamide,
useful as anti-HIV agents.

13 Claims, No Drawings

ANTI-VIRAL AROMATIC HYDRAZONES

FIELD OF THE INVENTION

This invention relates to novel aromatic hydrazones useful as anti-viral agents. In particular, this invention relates to novel aromatic hydrazones useful for the inhibition of the replication of HIV-1 and certain HIV-1 mutant strains.

BACKGROUND OF THE INVENTION

Retroviruses are viruses whose replication requires the transcription of viral RNA into DNA using the viral reverse transcriptase molecules attached to the viral RNA. This reverse transcription is the opposite of normal transcription which makes RNA from DNA.

Known retroviruses include HIV-1, HIV-2, the herpes family of viruses, HTLV-1 and cytomegalovirus (CMV). HIV, the virus which is presently believed to cause acquired immunodefiency syndrome (AIDS), is considered one of the principle threats to human life and health worldwide.

Various anti-HIV compounds have been proposed as useful in the treatment and prevention of AIDS, e.g., zidovudine (AZT), didanosine (ddI), zalcitabine (ddC), nevirapine, and dextran sulfate. However, none of the proposed compounds have been proven to be totally effective in the treatment or prevention of AIDS. For example, three of the currently FDA approved compounds for the treatment of AIDs, i.e., AZT, ddI and ddC, can all cause undesirable side effects in a patient, such as inhibition of bone marrow cell growth, and their effectiveness is limited by virus mutation.

U.S. Pat. No. 5,268,389 describes certain thiocarboxylate ester compounds useful for inhibiting the growth or replication of HIV.

It is the purpose of this invention to provide novel aromatic hydrazones, useful as anti-viral agents.

It is also the purpose of this invention to provide a method for inhibiting or preventing the growth or replication of HIV-1 and HIV-1 mutant strains using the novel aromatic hydrazones.

It is a further purpose of this invention to provide compositions comprising the novel aromatic hydrazones, useful for inhibiting or preventing the growth or replication of HIV-1 and HIV-1 mutant strains.

DESCRIPTION OF THE INVENTION

This invention relates to a compound of the formula

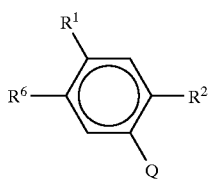

(I)

wherein Q is

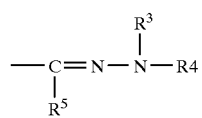

$R^1$ is hydrogen, halogen, $C_1$–$C_4$ alkyl or $C_1$–$C_4$ alkoxy;

$R^2$ is halogen, $C_1$–$C_4$ alkyl, $C_1$–$C_4$ alkoxy, $C_3$–$C_4$ alkenyloxy, $C_3$–$C_4$ alkynyloxy, mono-, di- or tri-halomethyl, trifluoromethoxy, $C_1$–$C_4$ alkylthio, $C_3$–$C_4$ branched alkylthio, nitro, or cyano;

$R^3$ and $R^4$ are, independently, linear or branched, $C_1$–$C_4$ alkyl, $C_1$–$C_4$ alkenyl, or $C_1$–$C_4$ alkynyl; or $R^3$ and $R^4$ together can form a heterocycle of the type whereby Q is

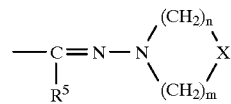

wherein

X is O, S, N—$R^w$, $CR^w R^w$;

each $R^w$ can be hydrogen or $C_1$–$C_4$ alkyl;

n and m are, independently, an integer of 1, 2 or 3 so as to form a minimum of a five membered ring;

$R^5$ is hydrogen or $C_1$–$C_4$ alkyl;

$R^6$ is $R^z$—NH—, wherein $R^z$ is

(A)

wherein $R^a$ and $R^b$ are independently hydrogen or $C_1$–$C_6$ alkyl; and $Z^1$ is O or S; or

(B)

wherein $Z^2$ is O or S; and $R^A$ is:

a) fully unsaturated, partially or fully reduced or substituted oxathiinyl, furanyl, dithiinyl, dioxinyl, thienyl, thiazolyl, oxazolyl, isoxazolyl, isothiazolyl, thiadiazoyl, pyrazolyl, pyrrolyl, imidazolyl, pyranyl, oxathiazinyl, oxadiazolyl, or indolyl;

b) substituted or unsubstituted, linear or branched $C_1$–$C_8$ alkyl, $C_2$–$C_8$ alkenyl, $C_2$–$C_8$ alkynyl, $C_2$–$C_8$ alkoxy, $C_2$–$C_8$ alkenyloxy, $C_2$–$C_8$ alkynyloxy, or $C_1$–$C_8$ mono- or di-alkylamino; $C_3$–$C_7$ cycloalkyl, $C_1$–$C_6$ alkyl, $C_3$–$C_7$ cycloalkenyl, unsubstituted or substituted by $C_1$–$C_6$ alkyl or $C_7$–$C_8$ phenylalkyl;

c) aryl, arylalkyl, aryloxyalkyl, or cycloalkylaryloxy wherein each alkyl moiety contains from 1 to 10 carbon atoms and each aryl moiety is naphthyl, phenyl or phenyl substituted by one or more halo, $C_1$–$C_8$ alkyl, carboxyl, $C_1$–$C_8$ haloalkyl, $C_1$–$C_8$ alkylthio, phenyl, nitro, amino, $C_1$–$C_8$ alkoxycarbonylamino, hydroxyl, acetyl, acetyloxy, phenoxy, $C_1$–$C_8$ alkoxycarbonyl or $C_1$–$C_8$ alkylcarbonyl;

d) $R^7$—W—, wherein

W is O, NH or $NR^f$ wherein $R^f$ is $C_1$–$C_4$ alkyl; and $R^7$ is linear or branched, unsubstituted or halo-substituted $C_1$–$C_8$ alkyl, $C_2$–$C_8$ alkenyl, $C_2$–$C_8$ alkynyl, $C_3$–$C_7$ cycloalkenyl unsubstituted or substituted by $C_1$–$C_6$ alkyl, unsubstituted phenyl or phenyl substituted by halo, $C_1$–$C_6$ alkyl, $C_1$–$C_6$ alkoxy, carboxyl, $C_1$–$C_8$ alkythio, phenyl, nitro, amino, hydroxyl, acetyl, acetyloxy, phenoxy, $C_1$–$C_8$ alkoxycarbonyl, or $C_1$–$C_8$ alkoxycarbonyl; furanylalkyl, tetrahydrofuranylalkyl, oxetanylalkyl, or oxiranylalkyl;

e) $R^8$—$W^1$—$R^e$—, wherein
$R^e$— is a linear or a branched $C_1$–$C_5$ alkylidene;
$W^1$ is O or S; and
$R^8$ is linear or branched $C_1$–$C_4$ alkyl;

f) $R^9R^{10}$—N—$R^e$—, wherein
$R^e$ is as defined above; and $R^9$ and $R^{10}$ are independently, linear or branched $C_1$–$C_4$ alkyl;

g)

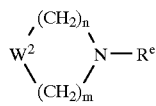

wherein
$R^e$ is as defined above;
$W^2$ is O, S, NH, $NR^{11}$ or $CR^{12}R^{13}$; wherein $R^{11}$ is linear or branched $C_1$–$C_4$ alkyl; $R^{12}$ and $R^{13}$ are independently hydrogen or linear or branched $C_1$–$C_4$ alkyl; and n' and m' are independently, 1,2 or 3;

h) $R^{14}$—$O_2$—C—$R^e$, wherein
$R^e$ is as defined above; and $R^{14}$ is linear or branched $C_1$–$C_6$ alkyl, $C_3$–$C_6$ alkenyl, or $C_3$–$C_6$ alkynyl or $C_3$–$C_7$ cycloalkyl or $C_3$–$C_7$ cycloalkenyl, unsubstituted, or substituted by $C_1$–$C_6$ alkyl;

i) U—$R^e$—, wherein
$R^e$ is as defined above; U is hydroxyl, acyloxy, aryloxy, arylsulphonyloxy, nitro, cyano or trimethylsilyl;

j) 1-adamantyl, 2-adamantyl or bornyl; or k) $Ar^1$—$R^e$—, wherein
$R^e$ is as defined above; and
$Ar^1$ is phenyl or phenyl substituted independently with one to three halogen, mono-, di- or trihalomethyl, nitro, $C_2$–$C_4$ alkyl, $C_3$–$C_4$ alkenyl, $C_1$–$C_4$ alkyloxy, $C_3$–$C_4$ alkenyloxy, or $C_3$–$C_4$ alkynyloxy, with the proviso that when $R_6$ is 2-methyl-3-furancarboxamide, then Q cannot be 4-morpholinyliminomethyl or 1-(4-methyl-piperazinyl) iminomethyl.

The compounds of this invention are useful for the inhibition of the replication of Human Immunodeficiency Virus-1 (HIV-1) and reverse transcriptase (RT) mutants thereof, in vitro and in vivo. The compounds are useful in the therapeutic or prophylactic treatment of diseases caused by HIV-1 and RT mutants thereof, such as acquired immune deficiency syndrome (AIDS).

This invention additionally relates to a pharmaceutical composition comprising a therapeutically effective amount of the compound of formula I and a pharmaceutically acceptable carrier.

This invention also relates to a method of treating HIV-1 infection in an afflicted host which comprises administering to the host a therapeutically effective amount of the compound of formula I.

DETAILED DESCRIPTION OF THE INVENTION

Preferred compounds are those compounds of formula I wherein $R^6$ is

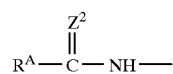

$Z^2$ is O or S; and
$R^A$ is
a) fully unsaturated, partially or fully reduced or substituted oxathiinyl, furanyl, dithiinyl, dioxinyl, thienyl, thiazoyl, oxazoyl, isoxazoyl, isothiazoyl, thiadiazolyl, pyrazolyl, pyrrolyl, pyranyl, oxathiazinyl, or oxadiazolyl;
b) linear or branched $C_1$–$C_5$ alkyl, $C_3$–$C_8$ alkenyl, $C_3$–$C_8$ alkynyl, $C_1$–$C_8$ alkoxy, $C_3$–$C_8$ alkenyloxy, $C_3$–$C_8$ alkynyloxy, or $C_1$–$C_8$ mono- or di-alkylamino; $C_3$–$C_6$ cycloalkyl or $C_3$–$C_6$ cycloalkenyl; or
c) phenyl or phenyl substituted by one or more halo, $C_1$–$C_8$ alkyl, $C_1$–$C_8$ haloalkyl, $C_1$–$C_8$ alkylthio, phenyl, amino, hydroxyl, carboxyl, acetyl, acetyloxy, $C_1$–$C_8$ alkoxycarbonyl, $C_1$–$C_8$ alkylcarbonyl or phenoxy; $C_7$–$C_8$ phenylalkyl or $C_7$–$C_8$ phenoxyalkyl, with the proviso that when $R^6$ is 2-methyl-3-furancarboxamide, then Q cannot be 4-morpholinyliminomethyl or 1-(4-methyl-piperazinyl) iminomethyl.

More preferred are those compounds of formula I wherein $R^6$ is

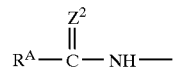

$Z^2$ is O or S; and
$R^A$ is
a) dihydro-3-oxathiinyl, furanyl, dihydrofuranyl, thienyl, pyrrolyl, dihydro-2-dithiinyl, or dihydro-2-dioxinyl, which can be substituted by one to three $C_1$–$C_4$ alkyl or $C_1$–$C_4$ alkoxyalkyl groups;
b) linear or branched $C_1$–$C_8$ alkyl, $C_2$–$C_8$ alkenyl, $C_3$–$C_8$ alkynyl, $C_1$–$C_8$ alkoxy, $C_3$–$C_8$ alkenyloxy, $C_3$–$C_8$ alkynyloxy or $C_1$–$C_8$ mono- or di-alkylamino; $C_3$–$C_8$ alkynyloxy or $C_1$–$C_8$ mono- or di-alkylamino; $C_3$–$C_6$ cycloalkyloxy or $C_3$–$C_6$ cycloalkenyloxy; or
c) phenyl or phenyl substituted by one or more halo, $C_1$–$C_8$ alkyl, $C_1$–$C_8$ haloalkyl, $C_1$–$C_8$ alkylthio, carboxyl, amino, $C_1$–$C_8$ alkoxycarbonyl, hydroxyl, $C_1$–$C_8$ alkylcarbonyl, phenyl or phenoxy, with the proviso that when $R^6$ is 2-methyl-3-furancarboxamide, then Q cannot be 4-morpholinyliminomethyl or 1-(4-methyl-piperazinyl) iminomethyl.

Particularly preferred compounds are the furan or thiophene derivatives of the compound of formula I wherein $R^6$ is:

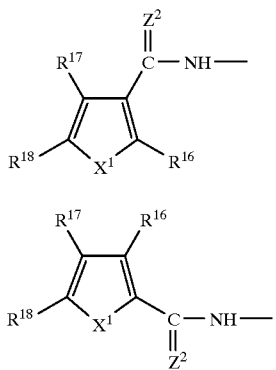

or

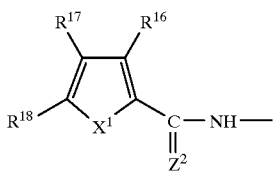

$Z^2$ is O or S;

$X^1$ is O or S;

$R^{16}$ is hydrogen, methyl, ethyl, 1,1-dimethylethyl, fluoro, carboxyl, acetamido, cyano, $C_1$–$C_6$ alkylthio, $C_1$–$C_6$ haloalkoxy, $C_1$–$C_6$ acyloxy, ($C_1$–$C_6$ alkoxy)carbonyl, or ($C_1$–$C_6$ alkyl)carbonyl; and $R^{17}$ and $R^{18}$ are independently, hydrogen or methyl, with the proviso that when $R^6$ is 2-methyl-3-furancarboxamide, then Q cannot be 4-morpholinyliminomethyl or 1-(4-methyl-piperazinyl)iminomethyl.

Most preferred compounds are compounds of the formula

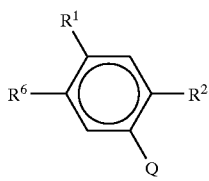

wherein Q is

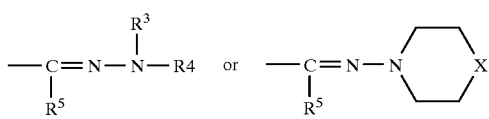

$R^1$ is hydrogen, halogen, $C_1$–$C_4$ alkyl or $C_1$–$C_4$ alkoxy, preferably, hydrogen;

$R^2$ is halogen, $C_1$–$C_4$ alkyl, $C_1$–$C_4$ alkoxy, $C_3$–$C_4$ alkenyloxy, $C_3$–$C_4$ alkynyloxy, mono-, di- or tri-halomethyl, trifluoromethoxy, $C_1$–$C_4$ alkythio, $C_3$–$C_4$ branched alkylthio, nitro, or cyano, preferably, halogen;

$R^3$ and $R^4$ are, independently, linear or branched, $C_1$–$C_4$ alkyl, $C_1$–$C_4$ alkenyl, or $C_1$–$C_4$ alkynyl, preferably, $C_1$–$C_4$ alkyl;

X is O, S, N—$R^w$, or $CR^wR^w$, preferably, O, N—$R^w$ or $CH_2$;

each $R^w$ can be hydrogen or $C_1$–$C_4$ alkyl, preferably, hydrogen or methyl;

$R^5$ is hydrogen or $C_1$–$C_4$ alkyl, preferably, hydrogen;

$Z^2$ is O or S; and $R^6$ is:

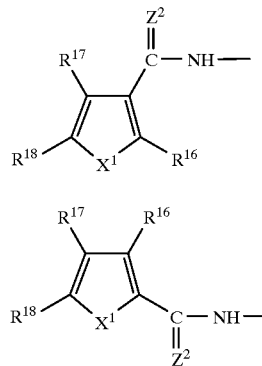

or

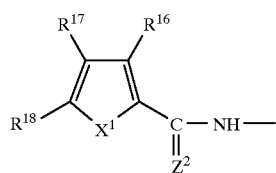

$Z^2$ is O or S;

$X^1$ is O or S;

$R^{16}$ is hydrogen, methyl, ethyl, 1,1-dimethylethyl, fluoro, carboxyl, acetamido, cyano, $C_1$–$C_6$ alkylthio, $C_1$–$C_6$ haloalkoxy, $C_1$–$C_6$ , acyloxy, ($C_1$–$C_6$ alkoxy)carbonyl, or ($C_1$–$C_6$ alkyl)carbonyl, preferably, hydrogen or methyl; and $R^{17}$ and $R^{18}$ are independently, hydrogen or methyl, with the proviso that when $R^6$ is 2-methyl-3-furancarboxamide, then Q cannot be 4-morpholinyliminomethyl or 1-(4-methyl-piperazinyl)iminomethyl.

Additionally preferred are the compounds of formula I wherein $R^6$ is:

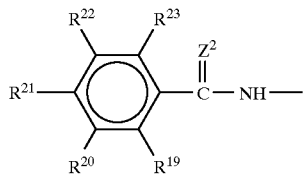

$Z^2$ is O or S;

$R^{19}$, $R^{20}$, $R^{21}$, and $R^{22}$ are independently, halogen or, preferably, hydrogen; and $R^{23}$ is hydrogen, halogen, $C_1$–$C_4$ alkyl, $C_1$–$C_4$ alkoxy, mono, di- or tri-haloalkoxy, $C_1$–$C_4$ haloalkyl, $C_1$–$C_4$ alkylthio, amino, $C_1$–$C_8$ alkylcarbonylamino, hydroxyl, acetyl, acetyloxy, or acetylamino, preferably hydrogen, methyl, ethyl, chloro, iodo, amino, bromo, fluoro, methylthio, methoxy, difluoromethoxy, or hydroxy.

Also preferred compounds are compounds in which $R^6$ is

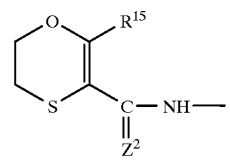

wherein $Z^2$ is O or S and $R^{15}$ is methyl, ethyl or propyl.

The compounds of this invention are useful for the inhibition of the growth or replication of retroviruses, particularly human immunodeficiency viruses such as HIV-1, in vitro and in vivo. The compounds are useful in the therapeutic or prophylactic treatment of diseases caused by retroviruses, such as AIDS or an HIV infection in a human or other mammal.

It is to be understood that the present invention encompasses all isomers, including positional or stereoisomers, of any compound of formula I exhibiting isomerism. It is also intended that any novel processes or intermediates for synthesizing said compounds be included within the scope of this invention.

GENERAL SYNTHETIC METHODS

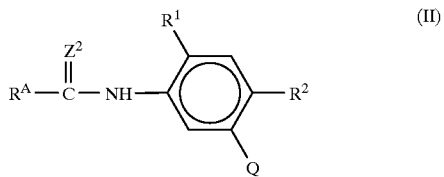
(II)

wherein $Z^2$ is O and $R^A$ is oxathiinyl, furanyl, thienyl, pyrrolyl, other heterocyclyl, or substituted phenyl, can be prepared from the appropriate carboxylic acid, $R^A$—COOH, and an aniline derivative of the formula

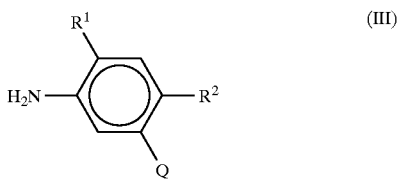
(III)

by employing one of the methods known in the art of amide bond formation. For example, the carboxylic acid can be converted to an acid halide, such as the acid chloride, $R^A COCl$, which can then be reacted with the aniline derivative to form the amide. The amide forming reaction is carried out in an appropriate solvent, such as methylene chloride, toluene, methyl ethyl ketone, tetrahydrofuran, dimethylformamide or acetonitrile, at a temperature of about 0° C. to about 100° C.

It is usually preferable to carry out the reaction in the presence of a base, such as triethylamine or pyridine. Other reactive derivatives of the carboxylic acid can be employed: for example the anhydride of the carboxylic acid or a mixed anhydride, such as alkoxycarbonyloxy derivative, can be reacted with the aniline derivative. Alternatively, the carboxylic acid and aniline derivative can be reacted directly in the presence of a condensing agent such as dicyclohexylcarbodiimide to form the amide.

The aniline derivatives can be prepared by reduction of the corresponding nitro compounds by well-known methods, for example with hydrogen and a catalyst, such as Raney nickel or platinum, or with metal-acid combination, such as iron or tin and hydrochloric or acetic acid.

In making the hydrazones of this invention, Q in the compound of formula II is a formyl group which prior to making the aniline as described above has to be protected as the ketal or acetal. Once the amide is formed, the formyl group is regenerated using mineral acid. Hydrazones are then made by the reaction of the above formyl group with hydrazine according to the equation:

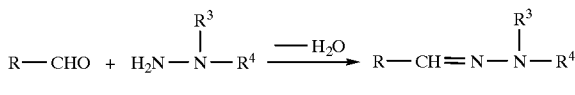

wherein R is the aromatic group attached to Q in formula II.

The compounds of the present invention can be administered by known conventional routes of administration such as orally, parenterally, intravenously, subcutaneously, sublingually, by inhalation spray, rectally, or topically in dosage unit formulations containing conventional non-toxic pharmaceutically acceptable carriers, adjuvants, and vehicles. Pharmaceutically acceptable carriers, adjuvants and vehicles useful in the composition of this invention can be found in standard pharmaceutical texts such as, e.g., *Remington's Pharmaceutical Sciences,* 16th Edition, Mack Publishing Company, Easton, Pa. (1980).

The therapeutically effective amount of the compounds of this invention that can be combined with the pharmaceutically acceptable carrier to produce a single dosage form will vary depending upon the age and condition of the host treated and the particular mode of administration. In general, the compounds of this invention are most desirably administered at a concentration level that will generally afford anti-virally effective results without causing any harmful or deleterious side effects.

While the compounds of this invention can be administered as the sole active pharmaceutical agents, the compounds can also be used in combination with one or more other pharmaceutical agents which are not deleterious to the activity of the compounds of this invention or whose combination with the compounds will not have a deleterious effect on the host treated.

The following examples are provided to illustrate the present invention.

EXAMPLES

Example 1

A. Preparation of 1,3-dioxolane, 2-(2-chloro-5-nitrophenyl)-

2-Chloro-5-nitrobenzaldehyde (18.6 g), ethylene glycol (18.6 ml), p-toluenesulfonic acid (monohydrate), (0.1 g), were refluxed in toluene (150 mL) for 3 hours. Water was removed azeotropically with a Dean-Stark trap. The reaction mixture was then transferred to seperatory funnel, washed with aqueous bicarbonate, water, dried (MgSO$_4$), filtered and evaporated producing 22.2 g of 2-(2- chloro-5-nitrophenyl-1,3-dioxolane as a white solid, m.p. 78–81° C.

B. Preparation of benzenamine, 4-chloro-3-(1,3-dioxolane-2-yl)-

To a refluxing, well-stirred suspension of iron powder (19.7 g, 100 mesh) in ethanol (56 mL), water (13.4 mL) and 36% hydrochloric acid (1.4 mL) was added 2-(2-chloro-5-nitrophenyl)-1,3-dioxolane (22.95 g) in portions over 15–30 minutes. The mixture was refluxed for 4 hours, filtered through Cellite, poured into water, extracted with ether, washed with aqueous sodium bicarbonate, water, dried (MgSO$_4$), filtered and evaporated to 19.2 g of 4-chloro-3-(1,3-dioxolane-2-yl)-benzenamine as a yellow oil.

C. Preparation of 3-furoic acid, 2-methyl-

To a stirred solution of water (400 mL) and conc. hydrochloric acid (40 mL) is added chloroacetaldehyde-dimethylacetal (300 g) and brought to reflux. The homogenous solution was then added to a stirred cooled solution of ethyl acetoacetate (260 g. 2 mol) in pyridine (500 mL). This reaction mixture was allowed to stir overnight at ambient temperature. The lower layer of the reaction mixture was then removed and combined with the methylene chloride (2×100 mL) extract of the upper layer after dilution with an equal volume of water. The combined organics were washed with 1N HCl (200 mL), and evaporation of the solvent left the crude ester. Hydrolysis of this ester was accomplished by refluxing for 1 hour in ethanol (100 mL) and sodium hydroxide (50 g) in water (700 mL). The reaction mixture was then poured into water/ice (3 L) and acidified with hydrochloric acid to give a cream precipitate which was collected on a filter, washed with water and dried, to produce 180 g of 2-methyl-3-furoic acid, m.p. 105–106° C.

D. Preparation of 3-furoyl chloride, 2-methyl-

Crude furoic acid (100 g) in thionyl chloride (500 mL) was refluxed for 3 hours. Excess thionyl chloride was removed. Distillation of the residual oil using a water pump, b.p. 67–69° C/12–15 mm, produced 100 g of 2-methyl-3-furoyl chloride as a pale yellow liquid which is stored in the dark.

E. Preparation of 3-furancarboxamide, N-[4-chloro-3 (1,3-dioxolane-2-yl) phenyl]-2-methyl- To 2-methyl-3-furoyl chloride (5.1 g) in ether (35 mL) was added dropwise solution of 4-chloro-2-(1,3- dioxolane-2-yl)benzamine (7 g), triethylamine (6.6 mL) in ether (35 mL). The resultant reaction mixture was stirred overnight at ambient temperature. Water was then added to the reaction mixture and the organic material was then extracted with ethyl acetate. The ethyl acetate extraction was washed successively with water, dilute hydrochloric acid (quickly), water, aqueous sodium bicarbonate and water. After drying, the ethyl acetate was removed to give 10 g of beige solid. Recrystallization of this solid from ethanol produced 7.8 g of N-[4-chloro-3(1,3-dioxolane-2-yl)phenyl]-2-methyl-3-furancarboxamide as a cream solid, m.p. 134–135° C.

F. Preparation of 3-furancarboxamide, N-(4-chloro-3-formylphenyl)-2-

N-[4-chloro-3-(1.3-dioxolane-2-yl)phenyl]-2-methyl-3-furancarboxamide (3.1 g) was stirred in acetone (15 mL) and 2N hydrochloric acid (7.5 mL) at the ambient temperature for 2 hours. The solvent was then evaporated and the remaining reaction mixture was poured into water and extracted with ethyl acetate. The organic layer was then washed with aqueous sodium bicarbonate and water, and then dried (MgSO₄), filtered and evaporated to 2.4 g of N-(4-chloro-3-formylphenyl)-2-methyl-3-furancarboxamide as a pale yellow solid, m.p. 180–182° C.

G. Preparation of 3-furancarboxamide, N-[[4-chloro-3-(dimethylhydrazono)methyl) phenyl]-2-methyl (Compound 1)

To the solution of 1,1-dimethylhydrazine (0.6 mL) in methanol (15 mL) was added, in portions, a suspension of N-(4-chloro-3-formylphenyl)-2-methyl-3-furancarboxamide (2 g) in methanol (30 mL) at such a rate that the temperature of the solution was maintained at −5° C. to 0° C. The resultant mixture was stirred overnight at ambient temperature. Acetic acid (0.1 mL) was then added to the reaction mixture which was then refluxed for 30 minutes, solvent was evaporated and the reaction mixture was poured into water and extracted with ethyl acetate. The organic layer was washed with water, dried (MgSO₄) filtered and evaporated to produce N-[4-chloro-3-[dimethylhydrazono)methyl]phenyl]- 2-methyl 3-furancarboxamide as a white solid, m.p. 109–111° C.

H. Preparation of 3-furancarbothioamide, N-[[4-chloro-3-(dimethylhydrazono)methyl]phenyl]-2-methyl (Compound 2)

A reaction mixture of N-[4-chloro-3-[dimethylhydrazono)methyl]phenyl]-2-methyl 3-furancarboxamide (1 g), sodium bicarbonate (1.8 g) and Lawesson's reagent (0.9 g) in toluene (20 mL) was refluxed for 3 hours. The reaction mixture was then cooled and filtered through a plug of neutral aluminum oxide and eluted with ether. Evaporation of the solvent produced 0.6 g of N-[4-chloro-3-[dimethylhydrazono)methyl]phenyl]-2-methyl-3-furancarbothioamide, m.p. 90–92° C.

Example 2

A. Preparation of 3-furancarboxamide, N-[4-chloro-3-(1-pyrrolidinylimino)methyl]-phenyl]-2-methyl (Compound 3)

To a chilled suspension of N-(4-chloro-3-formylphenyl)-2-methyl-3-furancarboxamide (1.6 g) in methanol (30 mL) and triethylamine (1.1 mL), 1-aminopyrrolidine hydrochloride (0.95 g) was added. The resultant mixture was stirred at ambient temperature overnight. The solvent was then evaporated, water was added and the organic layer was extracted with ethyl acetate. The ethyl acetate extraction was washed successively with water, diluted hydrochloric acid, aqueous sodium bicarbonate, and water. After drying, the solvent was removed to produce 1.7 g of N-[4-chloro-3-(1-pyrrolidinylimino)methyl]phenyl]-2-methyl-3-furancarboxamide as a white solid, m.p. 111–114° C.

B. Preparation of 3-furancarbothioamide. N-[4-chloro-3-(1-pyrrolidinylimino)methyl]phenyl]-2-methyl (Compound 4)

A reaction mixture of N-[4-chloro-3-(1-pyrrolidinylimino)methyl]phenyl]-2-methyl-3-furancarboxamide (1 g), sodium bicarbonate (2.5 g) and Lawesson's reagent (1.2 g) in toluene (25 mL) was refluxed for 3 hours. The reaction mixture was then cooled and filtered through a plug of neutral aluminum oxide and eluted with ether. Evaporation of the solvent gave an oil which was chromatographed on silica gel, eluted with methylene chloride. Evaporation of the solvent produced 0.6 g of 3-furancarbothioamide, N-[4-chloro-3-(1-pyrrolidinylimino)methyl]phenyl]-2-methyl as a yellow solid, m.p. 90–93° C.

Example 3

A. Preparation of 3-furancarboxamide, N-[4-chloro-3-[(4-morpholinylimino)methyl]phenyl]-2-methyl- To a chilled suspension of N-(4-chloro-3-formylphenyl)-2-methyl-3-furancarboxamide (2.0 g) in methanol (30 ml) was added 4-aminomorpholine (0.8 g). The resultant reaction mixture was stirred overnight. TLC analysis (methlyenechloride:ether, 5:1) of the reaction mixture showed a new spot and traces of substrate. The reaction mixture was stirred for another hour at 30° C. and then the reaction mixture was poured into water and extracted into ether/ethyl acetate. The extract was washed with water, dried (MgSO4), filtered, and evaporated to leave a solid. The solid was then covered with ether/ligroin and stirred for several hours and then collected on a filter to give 2.3 g of N-[4-chloro-3-[(4-morpholinylimino)methyl]phenyl]-2-methyl-3-furancarboxamide as an off-white solid, mp 121–123° C.

B. Preparation of 3-furancarbothioamide, N-[4-chloro-3-[(4-morpholinylimino)methyl]-phenyl]-2-methyl- (Compound No. 5)

A reaction mixture of N-[4-chloro-3-[(4-morpholinylimino)methyl]phenyl]-2-methyl-3-furancarboxamide (1.0 g), sodium bicarbonate (2.5 g), Lawesson's reagent (1.2 g) in toluene (25 ml) was heated at 85° C. for 4 hours. After cooling, the reaction mixture was passed through a plug of aluminum oxide, followed by elution with ether. Evaporation of the eluant gave 0.5 g of N-[4-chloro-3-[(4-morpholinylimino)methyl]phenyl]-2-methyl-3-furancarbothioamide as a yellow solid, mp 142–143° C.

Compounds 1, 2, 3, 4, and 5 gave satisfactory IR and/or NMR and/or Mass spectral analyses.

Example 4

Materials And Methods

Cells and Viruses

CEM cells were obtained from the American Tissue Cell Culture Collection (Rockville, Md.). HIV-1 (III$_B$) was originally obtained from the culture supernatant of persistently HIV-1-infected H9 cells and was provided by R. C. Gallo and M. Popovic (National Cancer Institute, National Institutes of Health, Bethesda, Md.). The selection and characterization of the HIV-1 RT mutant strains were done as follows: HIV-1/100-Ile ("100-Ile") was selected for resistance against TIBO R82150 as described in Balzarini et al, Virology 192: 246–253 (1993); HIV-1/103-Asn ("103-Asn") was selected for resistance against TIBO R82913 as described in Balzarini et al, Virology 192: 246–253 (1993); HIV-1/106-Ala ("106-Ala") was selected for resistance against nevirapine as described in Balzarini et al, J. Virol. 67: 5353–5359 (1993); HIV-1/138-Lys ("138-Lys") was selected for resistance against TSAO-m³T as described in Balzarini et al, Virology 192: 246–253 (1993) and Balzarini et al, Proc. Nat. Acad. Sci. U.S.A. 90: 6952–6956 (1993); HIV-1/181-Cys ("181-Cys") was selected for resistance against pyridinone L-697,661 as described in Balzarini et al, Virology 192: 246–253 (1993); and HIV-1/188-His ("188-His") was selected for resistance against HEPT as described in Balzarini et al, Mol. Pharmacol. 44: 694–701 (1993). 188-His was then further converted to HIV-1/188-Leu ("188-Leu") upon further passage in cell culture in the absence of the HEPT.

Antiviral Activity of the Test Compounds in Cell Cultures

CEM cells were suspended at ≈300,000 cells per mL of culture medium and infected with approximately 100 CCID$_{50}$ (CCID$_{50}$ being the 50% cell culture infective dose) of HIV-1 (III$_B$) or one of the HIV-1 RT mutant strains described above. Then 100 μL of the infected cell suspensions was added to 200 μL microtiter plate wells containing 100 μL of appropriate serial (5-fold) dilutions of the test compounds. The inhibitory effect of the test compounds on HIV-1 induced syncytium formation in CEM cells was examined microscopically on day 4 post infection. The 50% effective concentration (EC$_{50}$) was defined as the test compound concentration that inhibits syncytium formation in the HIV-1 infected cell cultures by 50%.

Results

Table 2 shows the activity of representative compounds of this invention against wild type HIV-1 and HIV-1 RT mutants.

TABLE 2

| Cmpd No. | EC$_{50}$ (μg/mL) | | | | | | |
|---|---|---|---|---|---|---|---|
| | HIV-1 III$_B$ | 138-Lys | 181-Cys | 106-Ala | 100-Ile | 103-Asn | 188-Leu |
| 1 | 0.225 | 1.600 | <2.00 | <2.00 | <2.00 | <2.00 | <2.00 |
| 2 | 0.008 | 0.040 | 0.130 | 0.065 | 0.140 | 0.650 | <2.00 |
| 3 | 0.325 | 1.600 | 1.000 | 1.300 | <2.00 | <2.00 | <2.00 |
| 4 | 0.015 | 0.080 | 0.100 | 0.100 | 0.330 | 0.340 | 4.500 |
| 5 | 0.130 | — | — | — | — | — | — |

What is claimed is:

1. A compound of the formula

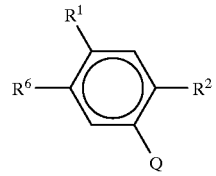

wherein

Q is

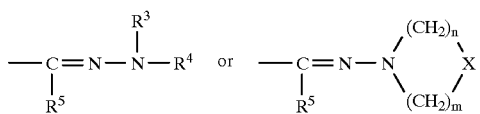

$R^1$ is hydrogen, halogen, $C_1$–$C_4$ alkyl or $C_1$–$C_4$ alkoxy;

$R^2$ is halogen, $C_1$–$C_4$ alkyl, $C_1C_4$ alkoxy, $C_3$–$C_4$ alkenyloxy, $C_3$–$C_4$ alkynyloxy, mono-, di- or trihalomethyl, trifluoromethoxy, $C_1$–$C_4$ alkylthio, $C_3$–$C_4$ branched alkylthio, nitro, or cyano;

$R^3$ and $R^4$ are, independently, linear or branched, $C_1$–$C_4$ alkyl, $C_2$–$C_4$ alkenyl, or $C_2$–$C_4$ alkynyl;

X is O or $CR^wR^w$;

$R^w$ is hydrogen or $C_1$–$C_4$ alkyl;

$R^5$ is hydrogen or $C_1$–$C_4$ alkyl;

$Z^2$ is O or S;

n and m are, independently, an integer of 1 or 2 so as to form a five- or six-membered ring; and $R^6$ is:

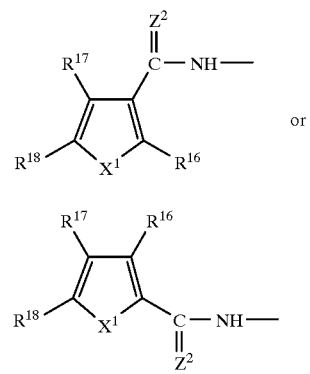

$Z^2$ is O or S;

$X^1$ is O or S;

$R^{16}$ is hydrogen, methyl, ethyl, 1,1-dimethylethyl, fluoro, carboxyl, acetamido, cyano, $C_1$–$C_6$ alkylthio, $C_1$–$C_6$ haloalkoxy, $C_1$–$C_6$ acyloxy, ($C_1$–$C_6$ alkoxy)carbonyl, or ($C_1$–$C_6$ alkyl)carbonyl; and $R^{17}$ and $R^{18}$ are independently, hydrogen or methyl, with the proviso that when $R^6$ is 2-methyl-3-furan-carboxamide, then Q cannot be 4-morpholinyliminomethyl.

2. A compound as recited in claim 1 wherein $R^1$ is hydrogen; $R^2$ is halogen; $R^3$ and $R^4$ are, independently, $C_1$–$C_4$ alkyl; X is O or $CH_2$; and $R^{16}$, $R^{17}$ and $R^{18}$ are independently, hydrogen or methyl.

3. A compound as recited in claim 2 wherein Q is

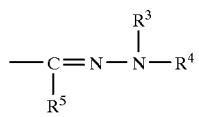

and $R^3$ and $R^4$ are, independently, $C_1$–$C_4$ alkyl.

4. A compound as recited in claim 2 wherein Q is

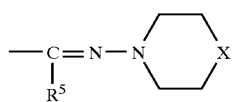

X is O or $CH_2$.

5. A pharmaceutical composition comprising a therapeutically effective amount of the compound as recited in claim 1 and a pharmaceutically acceptable carrier.

6. A pharmaceutical composition comprising a therapeutically effective amount of the compound as recited in claim 3 and a pharmaceutically acceptable carrier.

7. A pharmaceutical composition comprising a therapeutically effective amount of the compound as recited in claim 4 and a pharmaceutically acceptable carrier.

8. A method of treating HIV-1 infection in an afflicted host which comprises administering to the host a therapeutically effective amount of the compound as recited in claim 1.

9. A method of treating HIV-1 infection in an afflicted host which comprises administering to the host a therapeutically effective amount of the compound as recited in claim 3.

10. A method of treating HIV-1 infection in an afflicted host which comprises administering to the host a therapeutically effective amount of the compound as recited in claim 4.

11. A compound as recited in claim 2 wherein Q is

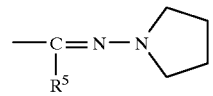

12. A pharmaceutical composition comprising a therapeutically effective amount of the compound as recited in claim 11 and a pharmaceutically acceptable carrier.

13. A method of treating HIV-1 infection in an afflicted host which comprises administering to the host a therapeutically effective amount of the compound as recited in claim 11.

* * * * *